United States Patent
Bratkovski et al.

(10) Patent No.: US 9,080,980 B2
(45) Date of Patent: Jul. 14, 2015

(54) SURFACE ENHANCED RAMAN SPECTROSCOPY EMPLOYING A NANOROD IN A SURFACE INDENTATION

(75) Inventors: Alexandre M Bratkovski, Mountain View, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/233,957

(22) PCT Filed: Jul. 27, 2011

(86) PCT No.: PCT/US2011/045611
§ 371 (c)(1),
(2), (4) Date: Jan. 21, 2014

(87) PCT Pub. No.: WO2013/015810
PCT Pub. Date: Jan. 31, 2013

(65) Prior Publication Data
US 2014/0176942 A1    Jun. 26, 2014

(51) Int. Cl.
G01J 3/44      (2006.01)
G01N 21/65     (2006.01)
G01N 21/01     (2006.01)

(52) U.S. Cl.
CPC .............. *G01N 21/658* (2013.01); *G01N 21/01* (2013.01)

(58) Field of Classification Search
USPC ..................... 356/301, 72–73, 244
See application file for complete search history.

(56) References Cited

U.S. PATENT DOCUMENTS

| | | |
|---|---|---|
| 5,250,167 A | 10/1993 | Adolf et al. |
| 5,532,006 A | 7/1996 | Lauterbur et al. |
| 6,271,278 B1 | 8/2001 | Park et al. |
| 6,538,089 B1 | 3/2003 | Samra et al. |
| 6,615,855 B2 | 9/2003 | Lopez et al. |
| 6,756,795 B2 | 6/2004 | Hunt et al. |
| 7,609,377 B2 | 10/2009 | Wu et al. |

(Continued)

FOREIGN PATENT DOCUMENTS

| | | |
|---|---|---|
| TW | 201111769 A | 4/2011 |
| TW | 201111771 A | 4/2011 |

(Continued)

OTHER PUBLICATIONS

Caldwell, J.D. et al., Plasmonic Nanopillar Arrays for Large-area High Enhancement Surface-enhanced Raman Scattering Sensors, (Research Paper), Apr. 11, 2011.

(Continued)

*Primary Examiner* — Abdullahi Nur
(74) *Attorney, Agent, or Firm* — North Shore Associates (57) ABSTRACT

A surface enhanced Raman spectroscopy (SERS) apparatus employs a nanorod in an indentation in a surface of a substrate. The SERS apparatus includes the nanorod having a tip at a free end opposite to an end of the nanorod that is supported by the substrate indentation. The indentation has a tapered profile and supports the nanorod at a bottom of the indentation. The free end of the nanorod extends away from the indentation bottom. The SERS apparatus further includes a Raman-active material at a surface of one or both of the nanorod and the indentation. The indentation and the nanorod facilitate one or both of production and detection of a Raman scattering signal emitted by an analyte in a vicinity of the nanorod and indentation.

15 Claims, 7 Drawing Sheets

(56) References Cited

U.S. PATENT DOCUMENTS

| | | | |
|---|---|---|---|
| 7,790,830 | B2 | 9/2010 | Edminston |
| 7,898,658 | B2 | 3/2011 | Moskovits et al. |
| 2006/0038990 | A1 | 2/2006 | Habib et al. |
| 2006/0252065 | A1 | 11/2006 | Zhao et al. |
| 2007/0166539 | A1 | 7/2007 | Zhao et al. |
| 2007/0196492 | A1 | 8/2007 | Ito et al. |
| 2010/0038086 | A1 | 2/2010 | Bunnel et al. |
| 2010/0063771 | A1 | 3/2010 | Miyata |
| 2010/0096334 | A1 | 4/2010 | Edminston |
| 2011/0063610 | A1* | 3/2011 | Ivanov et al. .............. 356/301 |

FOREIGN PATENT DOCUMENTS

| | | |
|---|---|---|
| WO | WO-2009114426 | 9/2009 |
| WO | WO-2010056258 | 5/2010 |

OTHER PUBLICATIONS

Gartia, M. R. et al., Rigorous Surface Enhanced Raman Spectral Characterization of Large-area High-unformity Silver-coated Tapered Sillca Nanopillar Arrays, Nanotechnology, Sep. 1, 2010, vol. 21, No. 39.

Hu et al., "Gold Nanofingers for Molecule Trapping Detection," J. Am. Chem. Soc., vol. 132, 2010, pp. 12820-12822.

Kim et al., "Study of Molecular Trapping Inside Gold Nanofinger Arrays on Surface-Enhanced Raman Substrates," J. Am. Chem. Soc., vol. 133, No. 21, 2011, pp. 8234-8239.

Linn, N.C. et al., Surface-enhanced Raman Scattering on Periodic Metal Nanotips with Tunable Sharpness, Nanotechnology, May 12, 2009, vol. 20, No. 22.

Ou et al., "Hot-Spot Engineering in Polygonal Nanofinger Assemblies for Surface Enhanced Raman Spectroscopy," Nano Letters, vol. 11, No. 6, 2011, pp. 2538-2542.

PCT International Search Report, Mar. 25, 2013, PCT Patent Application No. PCT/US2011/045611, Filed Jul. 27, 2011.

Schmidt, M. S. et al., Metal-coated Silicon Nonpillars with Large Raman Enhancement for Explosives Detection, Advanced Environmental, Chemical, and Biological Sensing Technologies VII, 2010, Orlando, Florida, USA.

Suzuki et al., "In-line aligned and bottom-up Ag nanorods for surface-enhanced Raman spectroscopy," Applied Physics Letters, vol. 88, 2006, pp. 203121-1 to 203121-3.

Tripp et al., "Novel nanostructures of SERS biosensing," Nanotoday, vol. 3, No. 3-4, Jun.-Aug. 2008, pp. 31-37.

Vernon, K.C. et al., Physical Mechanisms Behind the Sers Enhancement of Pyramidal Pit Substrates, Journal of Raman Spectroscopy, Oct. 2010, pp. 1106-1111, vol. 41, No. 10.

Wu et al., "Cones fabricated by 3D nanoimprint lithography for highly sensitive surface enhanced Raman spectroscopy," Nanotechnology, vol. 21, 2010, 255502, pp. 1-6.

Yao et al., "A complementary study of surface-enhanced Raman scattering and metal nanorod arrays," Pure Appl. Chem., vol. 72, No. 1, 2000, pp. 221-228.

Yuen et al., "Surface-Enhanced Raman Scattering: Principles, Nanostructures, Fabrications, and Biomedical Applications," Journal of Innovative Optical Health Sciences, vol. 1, No. 2, 2008, pp. 267-284.

\* cited by examiner

SURFACE ENHANCED RAMAN SPECTROSCOPY EMPLOYING A NANOROD IN A SURFACE INDENTATION

STATEMENT REGARDING FEDERALLY SPONSORED RESEARCH OR DEVELOPMENT

This invention has been made with government support under Contract No. HR0011-09-03-002. The government has certain rights in the invention.

CROSS-REFERENCE TO RELATED APPLICATION

This application is a U.S. National Stage Application and claims priority to PCT/US2011/045611, filed on Jul. 27, 2011, and entitled "SURFACE ENHANCED RAMAN SPECTROSCOPY EMPLOYING A NANOROD IN A SURFACE INDENTATION."

BACKGROUND

Detection and identification (or at least classification) of unknown substances have long been of great interest and have taken on even greater significance in recent years. Among methodologies that hold particular promise for precision detection and identification are various forms of spectroscopy, especially those that employ Raman scattering. Spectroscopy may be used to analyze, characterize and identify a substance or material using one or both of an absorption spectrum and an emission spectrum that results when the material is illuminated by a form of electromagnetic radiation (e.g., visible light). The absorption and emission spectra produced by illuminating the material determine a spectral 'fingerprint' of the material. In general, the spectral fingerprint is characteristic of the particular material facilitating identification of the material. Among the most powerful of optical emission spectroscopy techniques are those based on Raman-scattering.

Raman-scattering optical spectroscopy or simply Raman spectroscopy employs an emission spectrum or spectral components thereof produced by inelastic scattering of photons by an internal structure of the material being illuminated. These spectral components contained in a response signal (e.g., a Raman scattering signal) produced by the inelastic scattering may facilitate determination of the material characteristics of an analyte species including, but not limited to, identification of the analyte. Surface enhanced Raman-scattering (SERS) optical spectroscopy is a form of Raman spectroscopy that employs a Raman-active surface. SERS may significantly enhance a signal level or intensity of the Raman scattering signal produced by a particular analyte species. In particular, in some instances the Raman-active surface comprises regions associated with the tips of nanostructures such as, but not limited to, nanorods. The tips of the nanorods may serve as nanoantennas to concentrate an illumination field to further enhance the strength of the Raman scattering signal.

BRIEF DESCRIPTION OF THE DRAWINGS

The various features of examples in accordance with the principles described herein may be more readily understood with reference to the following detailed description taken in conjunction with the accompanying drawings, where like reference numerals designate like structural elements, and in which.

Certain examples have other features that are one of in addition to and in lieu of the features illustrated in the above-referenced figures. These and other features are detailed below with reference to the preceding drawings.

DETAILED DESCRIPTION

Examples according to the principles described herein facilitate surface enhanced Raman spectroscopy (SERS) employing a nanorod in a surface indentation. In particular, SERS is performed using a nanorod located within a pit or indentation in a surface of an underlying substrate. According to some examples, a combination of the surface indentation and the nanorod located therein may increase and in some examples, may significantly increase a Raman enhancement factor when compared to SERS that employs the nanorod alone. In some examples, the nanorod and surface indentation combination may facilitate launching plasmons on the nanorod with a focusing effect at one or both of a tip of the nanorod and an interface between the nanorod and a supporting surface of the surface indentation. A Raman enhancement factor in excess of $10^{11}$ may be achievable with the nanorod and surface indentation combination, according to some examples of the principles described herein.

Herein, a 'nanorod' is defined as an elongated, nanoscale structure having a length (or height) that exceeds by more than several times a nanoscale cross sectional dimension (e.g., width) taken in a plane perpendicular to the length (e.g., length is greater than about 10 times the width). In general, the length of the nanorod is much greater than the nanorod width or cross sectional dimension. In some examples, the length exceeds the cross sectional dimension (or width) by more than a factor of 5 or 10. For example, the width may be about 40 nanometers (nm) and the height may be about 400 nm. In another example, the width at a base of the nanorod may range between about 20 nm and about 100 nm and the length may be more than about 1 micrometer (μm). In another example, the nanorod may be conical with a base having a width ranging from between about 100 nm and about 500 nm and a length or height that may range between about one and several micrometers. In yet another example, the nanorod may have a diameter of between about 100 nm and about 200 nm (e.g., about 120 nm) with a length of between about 500 and about 600 nm (e.g., about 530 nm). The nanorod may have a metal tip (e.g., a gold cap) that is between about 50 nm and about 100 nm thick (e.g., about 70 nm thick).

In various examples, the nanorod or nanorods may be either provided by an additive process (e.g., grown or otherwise deposited on a surface), formed into a material of a surface, or produced from the surface material by a substantially subtractive process. For example, the nanorod(s) may be grown on the surface as nanowires using a vapor-liquid-solid (VLS) growth process. In another example, nanorod growth on the surface may employ one of a vapor-solid (V-S) growth process and a solution growth process. In another example, growth may be realized through directed or stimulated self-organization techniques such as, but not limited to, focused ion beam (FIB) deposition and laser-induced self assembly.

In other examples, one or more of nanoimprint lithography, nanoimprinting and nanoimprint embossing (e.g., using a polymer material) may be employed. Nanoimprinting and various embossing techniques act to rearrange the surface material to form the nanorod(s) substantially from the surface material. In other examples, the nanorod(s) may be produced by selective etching or another similar subtractive process such as, but not limited to, reactive ion etching, to remove surrounding material leaving behind the nanorod(s). In addition, various techniques used in the fabrication of micro-electromechanical systems (MEMS) and nano-electromechanical systems (NEMS) are applicable to the fabrication of the nanorod(s) and various other elements described herein.

Herein, an 'indentation' is defined as a depression purpose-formed in a surface. Further by definition herein, the indentation has an opening or lateral extent that is greater than a width of a nanorod located within the indentation. The lateral extent may be a width across an opening of the indentation at the surface into which the indentation is formed, for example. In some examples, the lateral extent is greater than twice the width of the nanorod. In other examples, the lateral extent is greater than four (4) to ten (10) times the width of the nanorod. For example, the width of the indentation may be between about 10 nm to greater than about 1000 nm. For example, when the nanorod has a width of 40 nm, the indentation may have a width of about 300 nm. In another example, the nanorod has a width of about 20 nm and the indentation has a width of about 400 nm. In other examples, the lateral extent is related to a length of the nanorod. For example, the lateral extent may be about one half the length of the nanorod.

In yet other examples, the lateral extent may be on the order of about the length of the nanorod.

In addition to the lateral size, the indentation has a depth, by definition. The depth is greater, and in some examples, much greater, than a surface roughness of the surface into which the indentation is purpose-formed. In particular, the depth and the lateral extent of the indentation together distinguish the indentation herein from features of the surface that may occur accidentally or naturally, for example. In some examples, the depth of the indentation is greater than about ten percent (10%) of the length of the nanorod located within the indentation. In some example, the depth is greater than 10% but less than a length of the nanorod. In other words, a portion of the nanorod extends above the surface into which the indentation is purpose-formed. For example, the depth may be between about 20% and about 80% of the nanorod length. In another example, the depth may be between about 30% and about 50% of the nanorod length. In some examples, the depth is less than about half of the length of the nanorod. The depth may be between about 20 nm and about 300 nm, for example.

In yet other examples, the depth is generally greater than a length of the nanorod. In other words, a tip of the nanorod is below the surface into which the indentation is purpose-formed. For example, the depth may be greater than about 110% of the nanorod length. In another example, the depth may be between about 105% and about 150% of the length. For example, the nanorod may have a length of between about 500 nm and 550 nm and the indentation may have a depth that is greater than 550 nm. A depth that is greater than a length of the nanorod may provide protection of the nanorod and nanorod tip from mechanical damage, for example.

The indentation may be formed (i.e., purpose-formed) by any number of circuit fabrication techniques including, but not limited to, etching (wet or dry), nanoimprint lithography and selective deposition. For example, a silicon substrate may be masked and exposed to a potassium hydroxide (KOH) solution to etch an exposed surface of the silicon and form the indentation. Etching a silicon substrate with KOH may produce an indentation with sloped or tapered sides and a flat bottom, for example. Plasma etching and especially reactive ion etching (RIE) may be employed in a directed fashion to produce a variety of specific tapered indentation profiles. Nanoimprint lithography may be employed variously in either subtractive or additive methods to form the indentation in a surface. Deposition, such as epitaxial deposition, may be used to build up the surface having the indentation, for example.

Further, as used herein, the article 'a' is intended to have its ordinary meaning in the patent arts, namely 'one or more'. For example, 'a nanorod' means one or more nanorods and as such, 'the nanorod' may also mean 'the nanorod(s)' herein. Also, any reference herein to 'top', 'bottom', 'upper', 'lower', 'up', 'down', 'front', 'back', 'first', 'second', 'left' or 'right' is not intended to be a limitation herein. Further, the designations 'first,' 'second' and so on as used herein do not imply any order of importance or any particular sequence, unless otherwise stated. The term 'about' as used herein means a value that is within the normal tolerances of the equipment used to measure the value, or in some examples, may mean that the value recited may differ by plus or minus 10%, or plus or minus 5%, or plus or minus 1%, unless otherwise stated. The term 'between' when used in conjunction with two numbers such as, for example, 'between 2 and 50' explicitly includes both of the numbers recited, in some examples. Moreover, examples herein are intended to be illustrative only and are presented for discussion purposes and not by way of limitation.

Figure 1A:
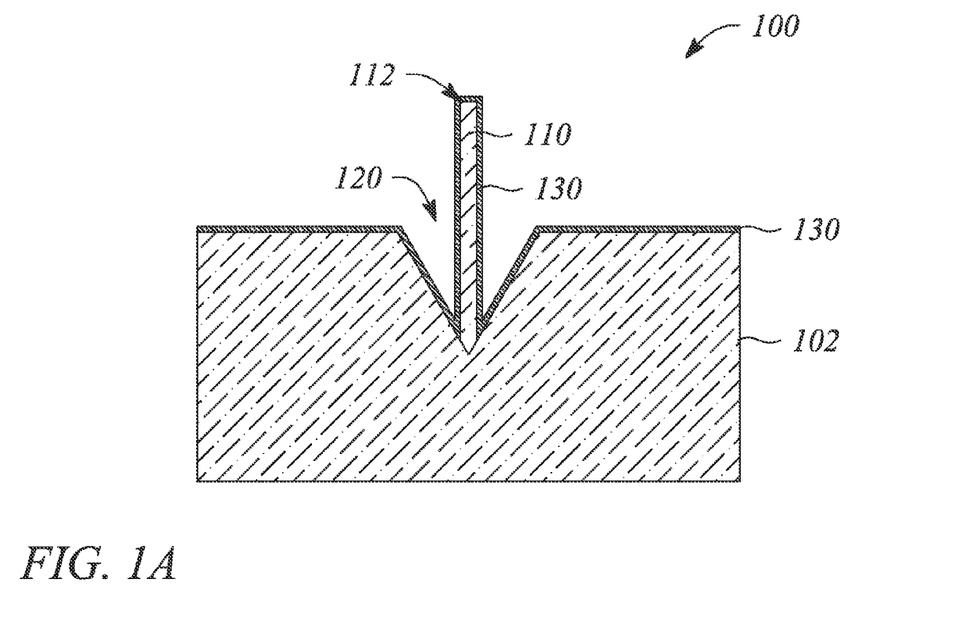
FIG. 1A illustrates a cross-sectional view of a surface enhanced Raman spectroscopy (SERS) apparatus, according to an example of the principles described herein.
Figure 1B:
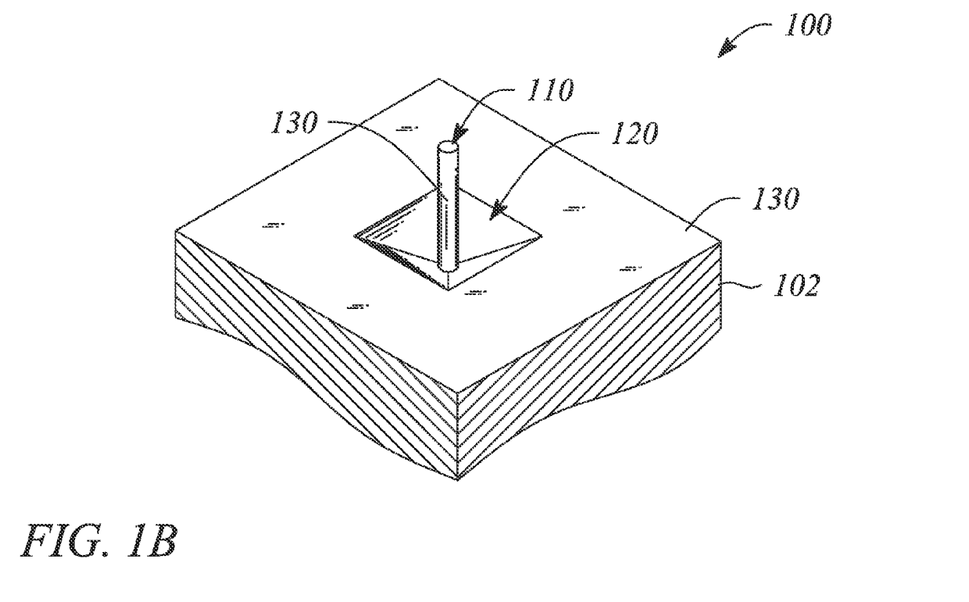
FIG. 1B illustrates a perspective view of a SERS apparatus, according to an example of the principles described herein.
Figure 1C:
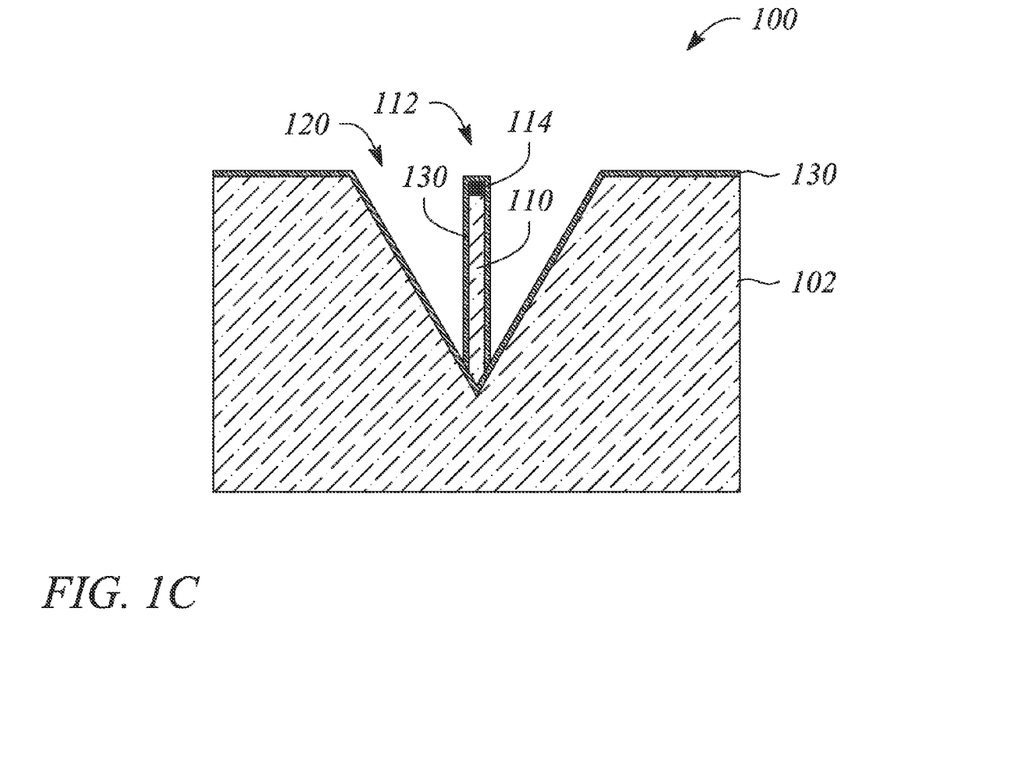
FIG. 1C illustrates a cross-sectional view of a SERS apparatus, according to another example of the principles described herein.

FIG. 1A illustrates a cross-sectional view of a surface enhanced Raman spectroscopy (SERS) apparatus 100, according to an example of the principles described herein. FIG. 1B illustrates a perspective view of a SERS apparatus 100, according to an example of the principles described herein. In particular, the SERS apparatus 100 is illustrated on a substrate 102. FIG. 1C illustrates a cross-sectional view of a SERS apparatus, according to another example of the principles described herein. In some examples, an analyte (not illustrated) may be introduced to and analyzed by the SERS apparatus 100. For example, the analyte may be introduced by flowing a gas or a liquid containing the analyte along or above the substrate 102 that supports the nanorod portion of the SERS apparatus 100. In some examples, the analyte is adsorbed onto a surface of the SERS apparatus 100. A Raman scattering signal produced by the adsorbed analyte is detected and analyzed to facilitate analysis (e.g., identification of) the analyte, according to various examples.

As illustrated, the SERS apparatus 100 comprises a nanorod 110 supported by the substrate 102. The nanorod 110 has a tip 112 at a free end opposite to a fixed end of the nanorod 110 that is supported by the substrate 102. A surface of the nanorod 110 and especially the tip 112 of the nanorod 110 may be configured to adsorb an analyte, according to some examples. In some examples, the nanorod 110 is rigidly attached to the substrate 102 at the fixed end. In other examples, the nanorod 110 is indirectly attached to the substrate 102 through an intermediate material or layer, for example.

According to some examples, the tip 112 may be either substantially flattened (as illustrated in FIG. 1A) or have a rounded (i.e., domed) shape. For example, the nanorod 110 may have a tip 112 that results naturally from a process (e.g., VLS growth) used to realize the nanorod 110. In other examples, the tip 112 may be further processed to impart a particular shape to the free end of the nanorod 110. The tips 112 of the nanorods 110 may be flattened using chemical-mechanical polishing, for example.

In some examples, the nanorod 110 may comprise a nanoparticle 114 attached to the free end in a vicinity of the tip 112. In some examples, a material of the nanoparticle 114 may differ from a material of the nanorod 110. For example, the tip 112 may include a rounded metal (e.g., gold) nanoparticle 114 that remains from nanorod growth, for example. In some of these examples, the nanoparticle 114 may be configured to one or both of enhance Raman scattering and facilitate selective analyte adsorption (e.g., by functionalization). In particular, in some examples, the nanoparticle 114 comprises a Raman-active material. For example, the nanoparticle may comprise a Raman-active material such as, but not limited to, gold, silver, platinum, aluminum and copper, having a nanoscale surface roughness, as described further herein.

In other examples (e.g., see FIG. 2C below), the tip 112 is substantially sharp. By 'sharp' it is meant that the tip 112 tapers from a cross sectional size of the nanorod 110 to an edge or a point at an end of the tip 112. The edge or the point generally has a relatively acute angle of inflection between surfaces of the tip 112 leading up to the edge or the point. In other words, a cross sectional size of the tip 112 in a vicinity of the end of the tip 112 (i.e., the edge or the point) is much smaller than an overall cross sectional size of the nanorod 110 away from the tip end. As such, the nanorod 110 having a tip 112 that is substantially sharp distinguishes it from other nanorods 110 having rounded or flat tips. A substantially sharp tip may provide a localized enhancement of an incident electromagnetic field, for example.

In some examples, the nanorod 110 has a generally columnar shape. The columnar portion may have either a curvilinear perimeter in cross section or a faceted perimeter in cross section. In particular, with respect to a cross section taken in a plane perpendicular to the long axis of the nanorod 110 and within the columnar portion, the columnar-shaped nanorod 110 may have a cross section that is characterized by either a curvilinear perimeter or a polygonal perimeter. For example, the columnar portion may have a triangular cross section, a rectangular cross section or a cross section with more than four sides. In another example, the columnar portion may have a perimeter that is circular, oval or curvilinear (e.g., a square with rounded corners). In some examples (not specifically illustrated), the nanorod may resemble a ribbon (e.g., a rectangular ribbon) having a cross sectional shape with one dimension that is much smaller than another, substantially orthogonal dimension (e.g., a thickness that is much less than a width).

Figure 2A:
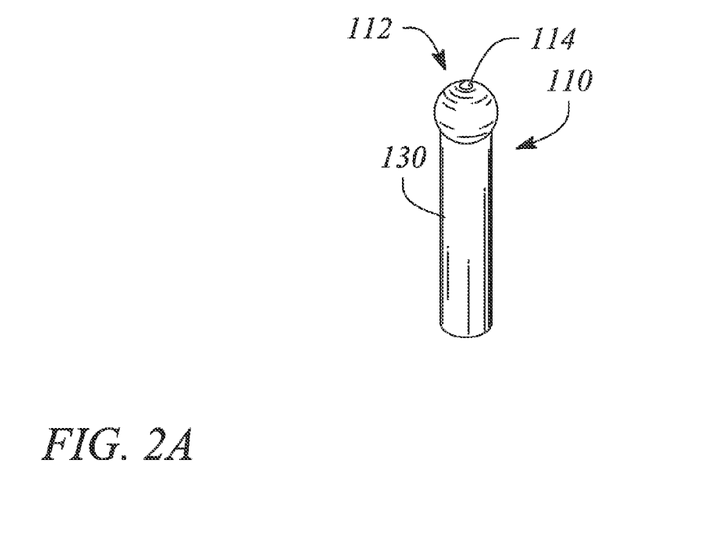
FIG. 2A illustrates a perspective view of a nanorod having a generally columnar shape, according to an example of the principles described herein.

FIG. 2A illustrates a perspective view of a nanorod 110 having a generally columnar shape, according to an example of the principles described herein. In particular, the columnar-shaped nanorod 110 illustrated in FIG. 1C has a generally circular cross-sectional shape. Further illustrated in FIG. 2A is a nanoparticle 114 on the tip 112 of the nanorod 110. The nanoparticle 114 may be gold, for example.

Figure 2B:
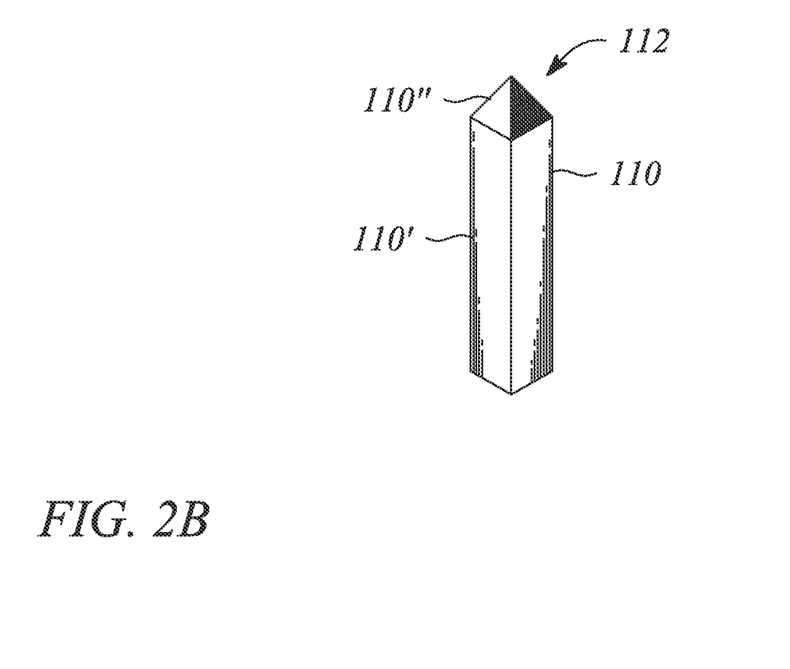
FIG. 2B illustrates a perspective view of another columnar-shaped nanorod, according to an example of the principles described herein.

FIG. 2B illustrates a perspective view of another columnar-shaped nanorod 110, according to an example of the principles described herein. A columnar portion 110' of the columnar-shaped nanorod 110 extends from the substrate to near the tip 112. A pyramidal portion 110" extends from the columnar portion 110' to the tip 112. In the example illustrated in FIG. 2B, the columnar-shaped nanorod 110 has a rectangular cross section within the columnar portion 110'.

Figure 2C:
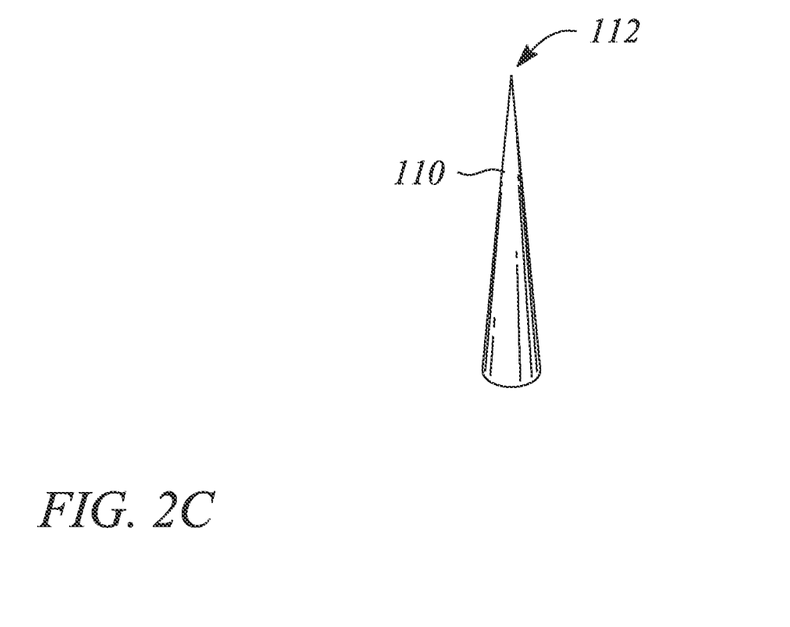
FIG. 2C illustrates a perspective view of a nanorod having a generally tapered shape, according to another example of the principles described herein.

In some examples, the nanorod 110 has a generally tapered shape. The tapered shape may be a relatively slight taper (e.g., less than about one to five degrees). In other examples, the taper may be more pronounced (e.g., greater than five degrees). FIG. 2C illustrates a perspective view of a nanorod 110 having a generally tapered shape, according to an example of the principles described herein. In particular, as illustrated in FIG. 2C, the tapered shape of the nanorod 110 is conical and more pronounced than one to five degrees. A perimeter of the conical nanorod 110 in a cross section orthogonal to the long axis of the nanorod is substantially circular, as illustrated.

In other examples, the tapered shape may have a curvilinear perimeter that is other than substantially circular when considering the perpendicular cross section. In other examples (not illustrated), the tapered shape may be generally faceted or pyramidal, for example having three, four, or more facets or sides. In addition, the nanorod 110 illustrated in FIG. 2C also has a sharp tip 112, for example. In some examples (not illustrated), the tapered nanorod may have a blunt, curved or even a substantially flat tip.

The nanorod 110, whether tapered or columnar, may have a long narrow profile that extends up from the support point at the substrate 102, according to some examples. In particular, the nanorod 110 may be greater than about three times longer than it is wide (or thick), according to some examples. In some examples, the nanorod 110 may be at least five times to ten times longer than it is wide. For example, the nanorod 110 may have a width between several nanometers (nm) and about 200 nm and a length that is between about 500 nm and about 1 micrometer (μm).

In some examples, the nanorod 110 comprises a plurality of nanorods 110. The plurality of nanorods 110 may be arranged in a bundle, for example. As used herein, a 'bundle' is defined as a relatively small grouping or a small array. For example, the bundle may comprise two, three, four, five, six or more nanorods 110, for example. The nanorods 110 of the bundle may be arranged as a digon, a trigon, a tetragon, a pentagon, a hexagon, and so on, according to various examples. In another example, a bundle may have up to about ten nanorods 110. In yet another example, the bundle may have less than about fifteen nanorods 110. Moreover, there may be a plurality of such bundles, in some examples.

Figure 2D:
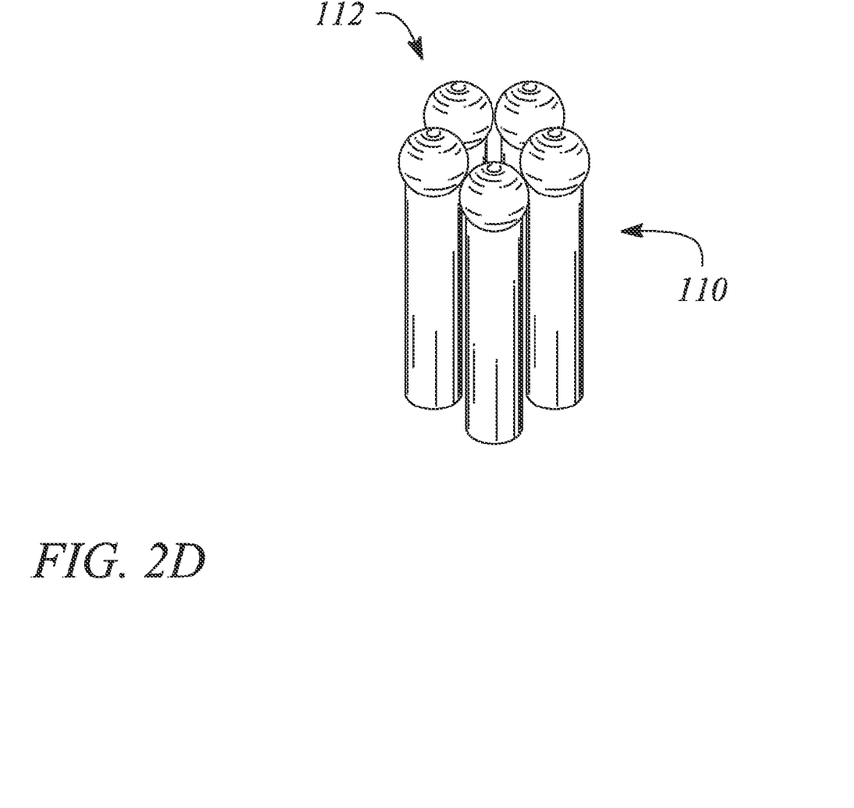
FIG. 2D illustrates a perspective view of a bundle of a plurality of nanorods, according to an example of the principles described herein.

FIG. 2D illustrates a perspective view of a bundle of a plurality of nanorods 110, according to an example of the principles described herein. The bundle illustrated in FIG. 2D comprises five nanorods 110. Further as illustrated, the plurality of nanorods 110 of the bundle is arranged as a pentagon.

In other examples, the plurality of nanorods 110 may be arranged in a larger array (not illustrated). A larger array may have several tens of nanorods, hundreds of nanorods or even more, for example. The array, including both small arrays (e.g., bundles) and large arrays, may include, but is not limited to, a linear array or one-dimensional (1-D) array or a two-dimensional (2-D) array (e.g., a rectilinear array, a circular array, etc.).

The nanorods 110 in either the bundle or the array may be either touching one another or spaced apart from one another. For example, tips 112 of the nanorods 110 in the bundle may be substantially touching or in physical contact with one another. Further, nanorods 110 in either the bundle or the array may be tilted toward one another. The tilting may facilitate contact between the tips of the nanorods 110, for example. A spacing between nanorods 110 of the plurality when spaced apart within the bundle or the array may be either regular (i.e., a periodic spacing) or irregular (e.g., a substantially random spacing). For example, the nanorods 110 of the plurality may be arranged in a pair of substantially parallel, regular, linear arrays.

In some examples, the nanorod 110 may comprise a semiconductor. For example, the semiconductor may comprise silicon (Si) or germanium (Ge) or an alloy of Si and Ge. In other examples, the semiconductor may comprise gallium arsenide (GaAs), indium gallium arsenide (InGaAs), and gallium nitride (GaN), or various other III-V, II-VI, and IV-VI compound semiconductors. In other examples, the nanorod 110 may comprise a plastic or a polymer such as, but not limited to, polymethylmethacrylate (PMMA), polystyrene, polycarbonate or related plastics. In yet other examples, the nanorod 110 may comprise a metal such as, but not limited to, gold, silver, platinum, other noble metals, aluminum copper, or an alloy or a combination of two or more metals.

Referring again to FIGS. 1A-1C, the SERS apparatus 100 further comprises an indentation 120 in a surface of the substrate 102. The surface indentation 120 has a tapered profile and supports the nanorod 110 at or substantially near a bottom of the indentation 120. The free end of the nanorod 110 generally extends away from the bottom of the indentation 120. In some examples, the nanorod 110 extends away from the bottom of the indentation 120 in a direction that is substantially perpendicular or normal to the surface of the substrate 102. For example, an angle between the nanorod 110 and the substrate surface may be within about ten degrees (10°) of perpendicular. In another example, the angle between the nanorod 110 and the substrate surface may be between about eighty degrees (80°) and ninety degrees (90°) (i.e., exactly perpendicular).

According to some examples, the nanorod 110 extends above the substrate surface 102, as illustrated in FIGS. 1A and 1B. For example, a depth of the indentation 120 may be less than about one half of a length of the nanorod 110. The depth may be between thirty percent (30%) and about fifty percent (50%) of the nanorod length, for example. In another example, the depth may be between about ten percent (10%) and about forty percent (40%) of the nanorod length. The nanorod 110 may be 500 nm in length and the indentation 120 may be about 200 nm deep, for example.

In other examples, the nanorod 110 is shorter than the depth of the indentation 120, as illustrated in FIG. 1C. In these examples, the tip 112 of the nanorod 110 is below (i.e., does not extend above) the substrate surface 102. A depth of the indentation 120 that is greater than a length of the nanorod 110 may protect the nanorod 110 and a functionalized surface thereof from mechanical abrasion and damage, for example. For example, the nanorod length may be less than about 90% of the depth. In another example the nanorod length may be just slightly shorter than the depth (e.g., the length is just less than 100% of the depth).

According to various examples, the tapered profile or cross-sectional shape of the surface indentation 120 may include, but is not limited to, a v-shaped profile, a parabolic profile and a semi-circular profile. By definition, a tapered profile is substantially any indentation profile or cross sectional shape having sloped walls. According to some examples, the sloped walls of the tapered indentation one or more of focuses, redirects and concentrates an incident electromagnetic field. For example, the sloped walls may assist in the formation and launching of surface plasmons produced by the incident electromagnetic field. The surface plasmons may concentrate the electromagnetic field in a vicinity of the sloped walls, for example. In other examples, the electromagnetic field may reflect from the sloped walls and be preferentially redirected toward the nanorod 110, for example. The redirection of the electromagnetic field may result in higher electromagnetic field intensity in a vicinity of the nanorod 110, for example. The concentration or higher electromagnetic field intensity may increase a SERS response or signal from an analyte collocated with the electromagnetic field, according to some examples.

Figure 3A:
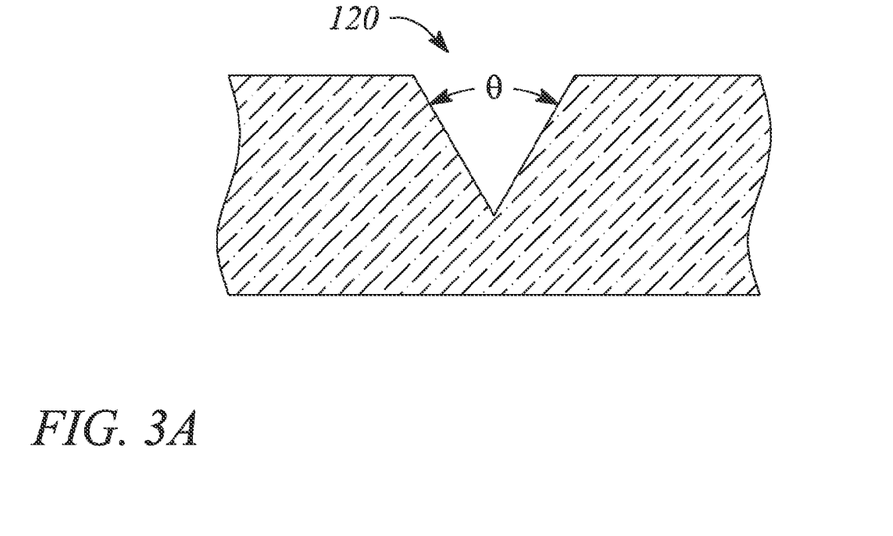
FIG. 3A illustrates a cross-sectional view of a tapered indentation having a v-shaped profile, according to an example of the principles described herein.

FIG. 3A illustrates a cross-sectional view of a tapered indentation 120 having a v-shaped profile, according to an example of the principles described herein. In some examples, an apex angle θ of the v-shaped profile may be between about thirty degrees (30°) and about one hundred twenty degrees (120°), for example. In other examples, the apex angle θ may be between about forty degrees (40°) and about ninety degrees (90°). For example, the apex angle θ may be about sixty degrees (60°). In another example, the apex angle may be either about fifty degrees (50°) or about seventy degrees (70°). In yet other examples, the apex angle θ is less than thirty degrees (30°) or greater than one hundred twenty degrees (120°).

In some example (e.g., as illustrated in FIG. 3A), the v-shaped profile is substantially symmetric about a vertical centerline such that a slope of opposite sloping walls is substantially similar to one another. In other examples (not illustrated), the v-shaped profile may be substantially asymmetric. For example, for an apex angle θ of about sixty degrees (60°), a first wall may have a slope of about twenty degrees (20°) with respect to the vertical centerline and a second wall may have a slope of about forty degrees (40°). A combination of a lateral size or width of the v-shaped profile and a slope of the wall or walls establishes a depth of the indentation 120, according to various examples.

The v-shaped tapered indentation 120 may comprise an inverse pyramidal indentation 120, as illustrated in FIG. 1B, according to an example of the principles described herein. The inverse pyramidal indentation 120 may have a v-shaped profile in two substantially orthogonal cross-sectional directions, for example. Moreover, the nanorod 110 may be located at a double apex of the inverse pyramidal indentation 120, for example. In another example (not illustrated), the v-shaped tapered indentation 120 may be an inverse conical indentation. An inverse conical indentation has a v-shaped profile in any cross section that passes through an apex of the 'v' of the v-shaped profile, for example. Again, the nanorod 110 may be located at the apex of the v-shaped profile of the inverse conical indentation 120, for example. The inverse pyramidal indentation 120 and the inverse conical indentation 120 may facilitate localization of hot spots in the SERS apparatus 100, for example.

Figure 3B:
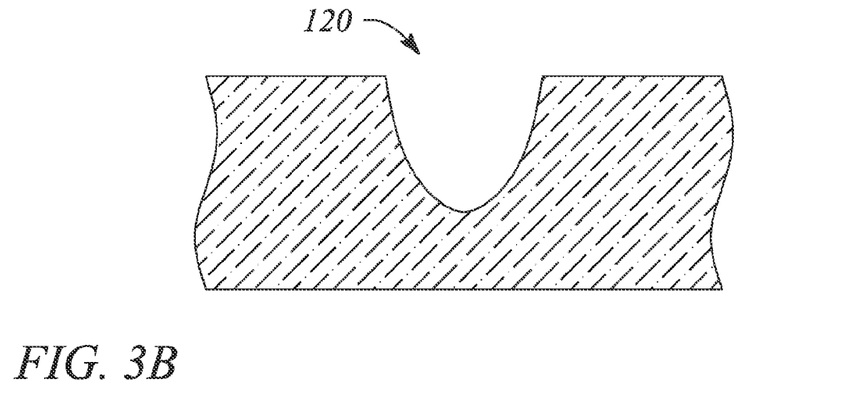
FIG. 3B illustrates a cross-sectional view of a tapered indentation having a parabolic profile, according to an example of the principles described herein.
Figure 3C:
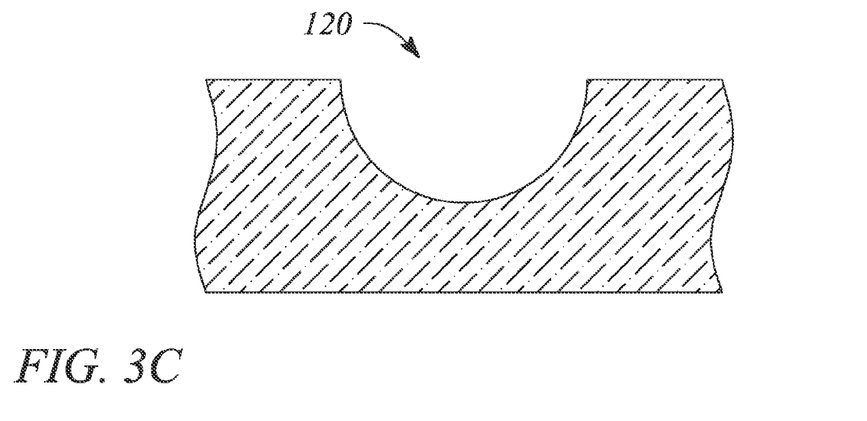
FIG. 3C illustrates a cross-sectional view of a tapered indentation having a semi-circular profile, according to an example of the principles described herein.

FIG. 3B illustrates a cross-sectional view of a tapered indentation 120 having a parabolic profile, according to an example of the principles described herein. A parabolic profile may substantially focus an incident electromagnetic field at a focus of a parabola that defines the parabolic profile, for example. In some examples (not illustrated), the foci may be substantially coincident with the nanorod 110 of the SERS apparatus 100 extending from the bottom of the tapered indentation 120 having the parabolic profile. FIG. 3C illustrates a cross-sectional view of a tapered indentation 120 having a semi-circular profile, according to an example of the principles described herein. The semi-circular profile is profile substantially defined by a section of a circle.

Figure 3D:
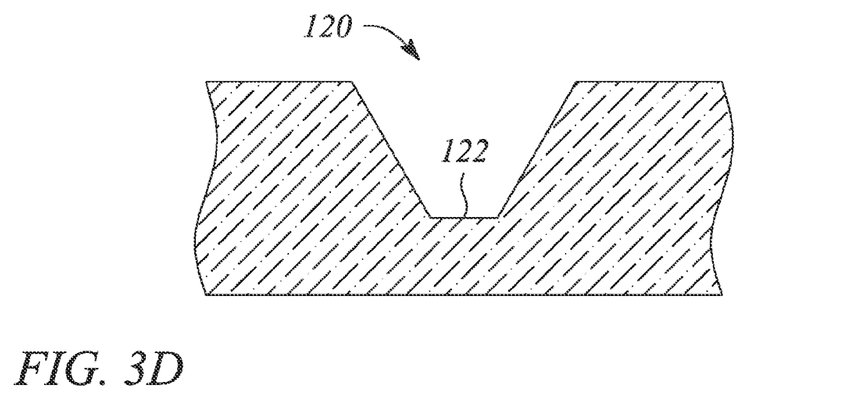
FIG. 3D illustrates a cross-sectional view of a tapered indentation having a v-shaped profile with a flat bottom, according to an example of the principles described herein.

In some examples, the tapered indentation 120 may have a horizontally oriented bottom portion (i.e., 'substantially flat bottom' for simplicity of discussion only). For example, the substantially flat bottom may be a surface that is substantially planar and parallel with the surface of the substrate 102. FIG. 3D illustrates a cross-sectional view of a tapered indentation 120 having a v-shaped profile with a horizontal or flat bottom 122, according to an example of the principles described herein. The flat bottom may facilitate formation by growth of deposition of the nanorod 110 at the bottom of the indentation 120, according to some examples.

Figure 4A:
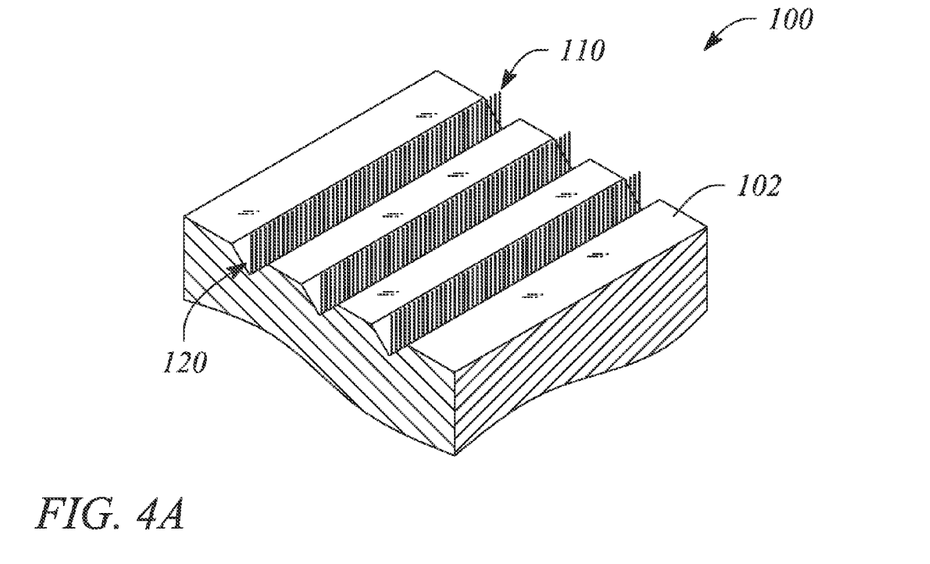
FIG. 4A illustrates a perspective view of a SERS apparatus with tapered indentations that form or are trenches, according to an example of the principles described herein.
Figure 4B:
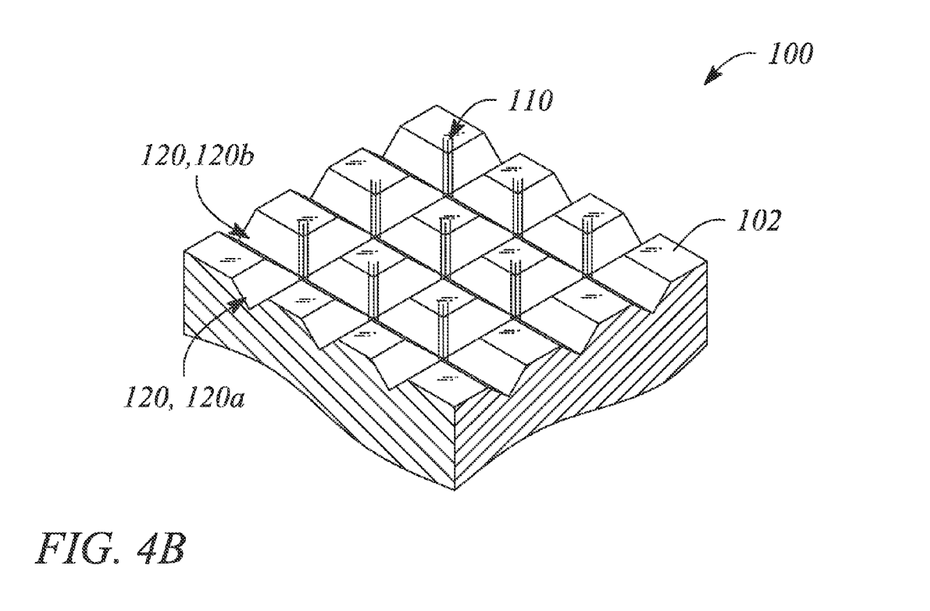
FIG. 4B illustrates a perspective view of a SERS apparatus with tapered indentations that form a grid of trenches, according to an example of the principles described herein.

FIG. 4A illustrates a perspective view of the SERS apparatus 100 with a tapered indention 120 that forms or is a trench 120, according to an example of the principles described herein. In particular, walls of the trench 120 have a v-shaped profile (e.g., perpendicular to a long dimension of the trench), as illustrated in FIG. 4B. Nanorods 110 may be arranged in an array along a length of the trench 120, for example. The array may be a 1-D array, for example.

FIG. 4B illustrates a perspective view of the SERS apparatus 100 with a tapered indention 120 that forms a grid of trenches, according to an example of the principles described herein. In particular, the tapered indentation 120 comprises a first plurality of substantially parallel trenches 120a and a second plurality of substantially parallel trenches 120b. The first plurality of parallel trenches 120a may be oriented substantially perpendicular to the second plurality of parallel trenches 120b, for example. Nanorods 110 may be arranged along a length of one or both first plurality of parallel trenches 120a and second plurality of parallel trenches 120b, according to some examples (not illustrated). In other examples, bundles of nanorods 110 may be substantially located at intersections of the first and second plurality of parallel trenches 120a, 120b (e.g., as illustrated in FIG. 4C).

Referring again to FIG. 1A, the SERS apparatus 100 further comprises a Raman-active material 130. The Raman-active material 130 is at a surface of one or both of the nanorod 110 and the indentation 120, according to various examples. In particular, in some examples, the Raman-active material 130 is a material layer on a surface of one or both of the nanorod 110 and the indentation 120, as illustrated in FIG. 1A. For example, after indentation 120 is formed in the substrate surface and the nanorod 110 is provided in the indentation 120, the Raman-active material 130 may be deposited as a layer on respective surfaces of the nanorod 110 and the indentation 120. In other examples, one or both of the nanorod 110 and the substrate 102 comprise the Raman active material 130. For example, the nanorod 110 may be fabricated from the Raman active material 130. In another example, the substrate 102 into which the indentation 120 projects comprises the Raman active material 130. As such, the Raman active material is at the surface of the indentation 120 once the indentation 120 is formed or otherwise provided in the surface of the substrate 102.

By definition herein, a Raman-active material is a material that facilitates Raman scattering and the production or emission of a Raman scattering signal from an analyte adsorbed on or in a surface layer of the material during Raman spectroscopy. Examples of Raman-active materials include, but are not limited to, gold, silver, platinum, other noble metals, aluminum or copper, as mentioned above. In some examples, the Raman-active materials comprise a surface or surface layer(s) having nanoscale surface roughness (e.g., generally coated with metal). Nanoscale surface roughness is generally provided by nanoscale surface features on the surface of the layer(s). Nanoscale surface roughness may be produced spontaneously during deposition of the Raman-active material layer(s) (e.g., gold deposition), for example. In another example, surface roughness may be intentionally induced (e.g., using a laser beam).

In some examples, one or both of the nanorod 110 and the indentation 120 (i.e., a surface of the indentation 120), or at least a portion or portions thereof, is coated with a layer of the Raman-active material 130. For example, the nanorods 110 and the indentation surface may be coated using evaporation or sputtering with a layer of a Raman-active metal. In some examples, the coating layer of Raman-active material is relatively thin compared to a width or thickness of the nanorod 110. For example, the Raman-active material layer may have a width or thickness that is less than about 1/10 of the width of the nanorod 110. The Raman-active material 130 layer may be about 5 nm to about 10 nm wide, for example.

In some examples, the Raman-active material 130 layer may be confined to or localized in a vicinity of one or both of the tip 112 of the nanorod 110 and an interface between the nanorod 110 and the indentation surface. In particular, the Raman-active material may be localized in areas of the nanorod 110 and the indentation 120 that may experience a relatively most intense electromagnetic field when the SERS apparatus 100 is illuminated, for example. In other examples, the Raman-active material 130 may extend along more of a length of the nanorod 110 than just a vicinity of the tip 112. For example, a majority of the length, or in some examples, an entire length, of the nanorod 110 may be coated with the Raman-active material 130 layer, according to some examples. In some examples, the Raman-active material layer (e.g., metal) may be annealed or otherwise treated to increase nanoscale surface roughness of the Raman-active material layer after deposition. Increasing the surface roughness may enhance Raman scattering from an adsorbed analyte, for example. In some examples, the Raman-active material layer comprises a layer or layers of nanoparticles. For example, a monolayer of gold nanoparticles may be used to coat one or both of the nanorod 110 and the surface of the indentation to produce the Raman-active material layer. The layer of nanoparticles may provide a nanoscale roughness that enhances Raman scattering, for example.

In some examples, a surface of one or both of the nanorod 110 and the indentation 120 may be functionalized to facilitate adsorption of the analyte. For example, the tip 112 or a portion of the nanorod 110 in a vicinity of the tip 112 may be functionalized (not illustrated) with a binding group to facilitate binding with a specific target analyte species. A surface of the Raman-active material 130 at the tip 112 of the nanorod 110 may be functionalized, for example. In another example, a surface of the indentation may be functionalized. The functionalized surface may provide a surface to which a particular class of analytes is attracted and may bond or be preferentially adsorbed. The functionalized surface may selectively bond with one or more of protein, DNA, RNA, and various other species (including hazardous species), for example.

Figure 5:
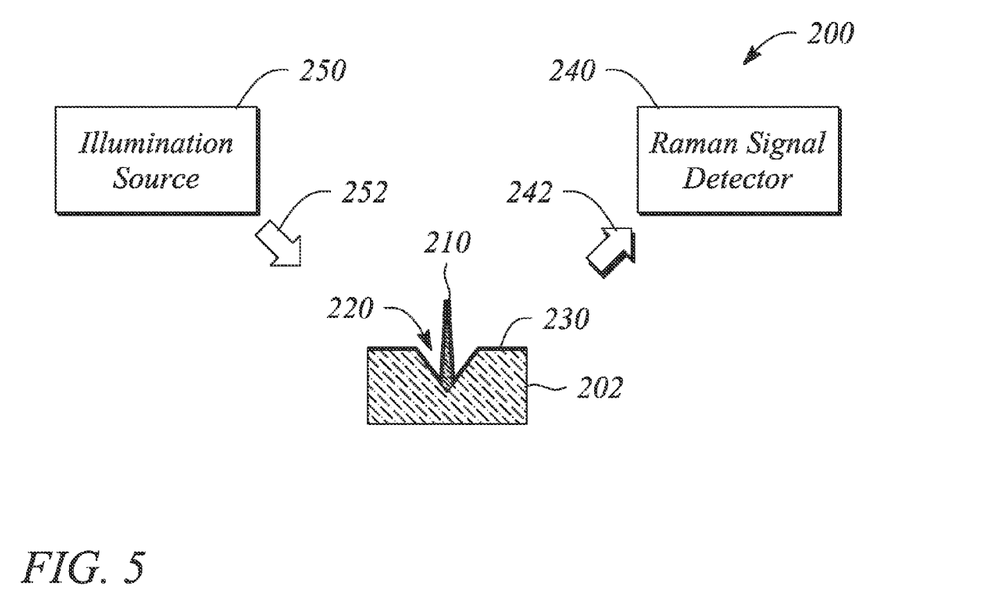
FIG. 5 illustrates a block diagram of a nanorod surface enhanced Raman spectroscopy (SERS) system, according to an example of the principles described herein.

FIG. 5 illustrates a block diagram of a nanorod surface enhanced Raman spectroscopy (SERS) system 200, according to an example of the principles described herein. According to some examples, the nanorod SERS system 200 detects and analyzes an analyte using a Raman scattering signal 242 emitted by an analyte. In particular, an active configuration of the nanorod SERS system 200 may facilitate detection of the Raman scattering signal emitted by the analyte.

As illustrated in FIG. 5, the nanorod SERS system 200 comprises a nanorod 210 within a tapered indentation 220 in a surface of a substrate 202. The nanorod 210 has a tip at a free end opposite to an end of the nanorod 210 that is supported by a bottom of the tapered indentation 220. One or both of the nanorod 210 and a surface of the tapered indentation 220 are configured to adsorb the analyte, according to some examples.

In some examples, the nanorod 210 is substantially similar to the nanorod 110, described above with respect to the SERS apparatus 100. In particular, the nanorod 210 may comprise one or more nanorods 210, including bundles and arrays of nanorods, according to some examples. In some examples, the tapered indentation 220 is substantially similar to the indentation 120 described above with respect to the SERS apparatus 100. For example, the tapered indentation 220 may have any of a number of taper profiles, as described above. In particular, the tapered indentation 220 may have one of a parabolic profile and a v-shaped profile, according to some examples. The tapered indentation 220 may be an inverse pyramidal indentation having the v-shaped profile, for example. In addition, the tapered indentation 220 may have a depth of less than a length of the nanorod 210, for example.

The nanorod SERS system 200 illustrated in FIG. 5 further comprises a Raman-active material 230. The Raman-active material 230 is at a surface of one or both of the nanorod 210 and the tapered indentation 220, according to various examples. The Raman-active material 230 may be configured to adsorb the analyte instead of or in addition to the analyte being adsorbed by a surface of one or both of the nanorod 210 and the tapered indentation 220. According to some examples, the Raman-active material 230 may be substantially similar to the Raman-active material 130 described above with respect to the SERS apparatus 100.

As illustrated in FIG. 5, the nanorod SERS system 200 further comprises a Raman signal detector 240. The Raman signal detector 240 is configured to receive the Raman scattering signal 242 from the analyte adsorbed on one or both of the nanorod 210 and the tapered indentation 220. The Raman signal detector 240 may include, but is not limited to, detectors that employ or comprise photomultipliers, charge-coupled devices (CCD) as well as various types of spectrographs. Spectrographs may include, but are not limited to axial transmissive (AT) spectrographs and Czerny-Turner (CT) monochromators, for examples. Fourier transform (FT) spectroscopy or FT may also be employed in the Raman signal detector 240, according to some examples.

In some examples, the nanorod SERS system 200 further comprises an illumination source 250. The illumination source 250 is configured to illuminate one or both of the nanorod 210 and the tapered indentation 220. The illumination source 250 may emit an illumination signal 252 comprising a beam of electromagnetic (EM) radiation (e.g., an optical beam or optical signal) having a frequency that stimulates emission of the Raman scattering signal 242 by the adsorbed analyte, for example. In some examples, the illumination source 250 may comprise a laser and the illumination signal 252 may comprise a laser beam. In other examples, the illumination source 250 may be other means for generating the EM radiation (e.g., a light emitting diode or an incandescent light source).

Figure 6:
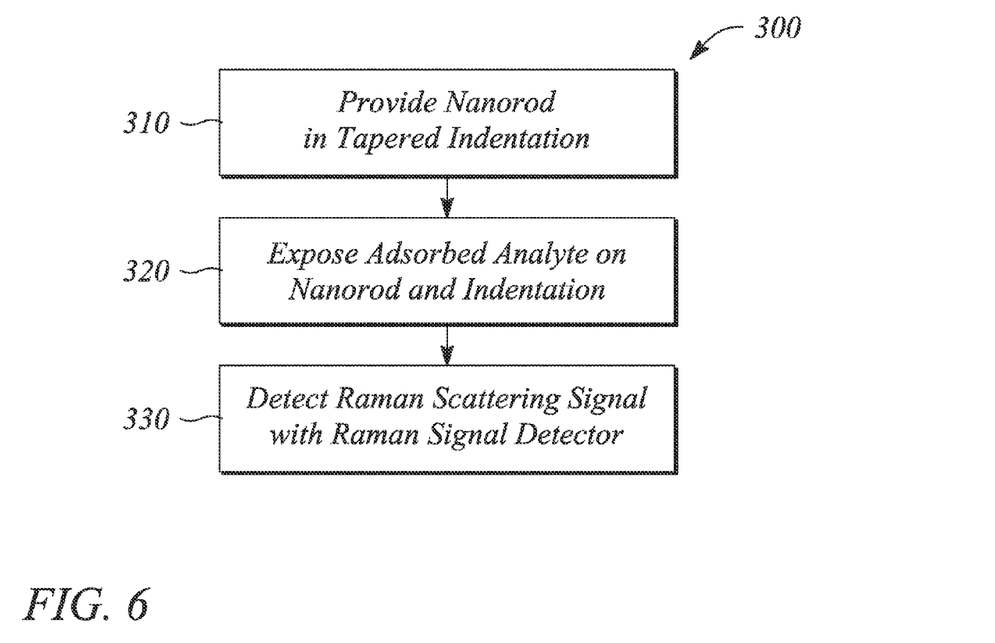
FIG. 6 illustrates a flow chart of a method of surface enhanced Raman spectroscopy (SERS), according to an example of the principles described herein.

FIG. 6 illustrates a flow chart of a method 300 of surface enhanced Raman spectroscopy (SERS), according to an example of the principles described herein. The method 300 of SERS comprises providing 310 a nanorod in a tapered indentation in a surface of a substrate. The provided nanorod may be supported at a bottom of the tapered indentation, for example. Each nanorod has a tip at a free end opposite an end of the nanorod that is supported by the indentation bottom. One or both of a surface of the nanorod and a surface of the tapered indentation comprises a Raman-active material, as provided 310. In some examples, the provided 310 nanorod is substantially similar to the nanorods 110, 210 described above with respect to either of the SERS apparatus 100 or the SERS system 200. In some examples, the tapered indention in which the nanorod is provided 310 is substantially similar to the indentation 120, 220 described above with respect to either of the SERS apparatus 100 or the SERS system 200. Likewise, the Raman-active material at the surface of one or both of the nanorod and the tapered indentation may be substantially similar to the Raman-active material 130, 230 described above with respect to either of the SERS apparatus 100 or the SERS system 200.

The method 300 of SERS further comprises exposing 320 an analyte adsorbed on one or both of the surface of the tapered indentation and the surface of the nanorod to an illumination signal to produce a Raman scattering signal. The tapered indentation and the nanorod may facilitate one or both of production and detection of the Raman scattering signal emitted by the adsorbed analyte, according to various examples. In some examples, exposing 320 the analyte is provided by an illumination source such as, but not limited to, a laser that produces an optical beam (i.e., an EM beam). According to some examples, the method 300 of SERS further comprises detecting 330 the Raman scattering signal from the adsorbed analyte using a Raman signal detector. In some examples, the Raman signal detector is substantially similar to the Raman signal detector 240 described above with respect to the SERS system 200.

In some examples, providing 310 the nanorod in the tapered indentation comprise forming the tapered indentation in the substrate surface. The tapered indentation may be formed by one or more of etching, nanoimprinting and depositing, for example. In some examples, providing 310 the nanorod in the tapered indentation may further comprise forming the nanorod within the tapered indentation. For example, the nanorod may be formed by growing the nanorod (e.g., using VLS growth) from the bottom of the tapered indentation. In another example, the nanorod is formed by depositing the nanorod using nanoimprinting.

Thus, there have been described examples of a SERS apparatus, a SERS system and a method of SERS using a nanorod in a surface indentation. It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A surface enhanced Raman spectroscopy (SERS) apparatus comprising:
   a nanorod having a tip at a free end opposite to an end of the nanorod that is supported by a substrate;
   an indentation in a surface of the substrate, the indentation having a tapered profile and supporting the nanorod at a bottom of the indentation, the free end of the nanorod extending away from the indentation bottom; and
   a Raman-active material at a surface of both of the nanorod and the indentation, a combination of a shape and the Raman-active material surface of the indentation to redirect and concentrate an incident electromagnetic field, the electromagnetic field being incident from a direction toward which the nanorod extends,
   wherein the redirected and concentrated incident electromagnetic field is to facilitate one or both of production and detection of a Raman scattering signal emitted by an analyte in a vicinity of the nanorod and indentation.

2. The SERS apparatus of claim 1, wherein the nanorod comprises a plurality of nanorods arranged in a bundle.

3. The SERS apparatus of claim 1, wherein the nanorod has a columnar shape, the nanorod further comprising a nanoparticle at the free end of the nanorod.

4. The SERS apparatus of claim 1, wherein the indentation has one of a parabolic profile and a v-shaped profile.

5. The SERS apparatus of claim 4, further comprising a trench, the trench comprising the indentation having walls with a v-shaped profile, the trench having a length and a width, the length being greater than the width.

6. The SERS apparatus of claim 1, wherein a depth of the indentation is less than half of a length of the nanorod.

7. The SERS apparatus of claim 1, wherein the Raman-active material comprises a noble metal.

8. A nanorod SERS system comprising the SERS apparatus of claim 1, the nanorod SERS system further comprising:
   an illumination source to illuminate the nanorods and to provide the incident electromagnetic field, the illumination from the illumination source to produce the Raman scattering signal; and
   a Raman signal detector to detect the Raman scattering signal emitted by the analyte.

9. A surface enhanced Raman spectroscopy (SERS) system comprising:
   a nanorod within a tapered indentation in a surface of a substrate, the nanorod having a tip at a free end opposite to an end of the nanorod that is supported at a bottom of the tapered indentation, wherein the free end extends away from the bottom;
   a Raman-active material at a surface of one or both of the nanorod and the tapered indentation, a combination of a shape and the Raman-active material surface of the indentation to redirect and concentrate an incident electromagnetic field, the electromagnetic field being incident from a direction toward which the nanorod extends; and
   a Raman signal detector to receive a Raman scattering signal emitted by an adsorbed analyte on one or both of the nanorod and the tapered indentation,
   wherein the redirected and concentrated incident electromagnetic field facilitates one or both of production and detection of the Raman scattering signal emitted by the adsorbed analyte.

10. The SERS system of claim 9, wherein the tapered indentation is an inverse pyramidal indentation having a v-shaped profile.

11. The SERS system of claim 9, wherein the tapered indentation has a depth that is greater than a length of the nanorod.

12. The SERS system of claim 9, wherein the tapered indentation has one of a parabolic profile and a v-shaped profile.

13. A method of surface enhanced Raman spectroscopy (SERS), the method comprising:
   providing a nanorod in a tapered indentation in a surface of a substrate, the nanorod being supported at a bottom of the tapered indentation and extending in an upward direction away from the bottom, both of a surface of the nanorod and a surface of the tapered indentation comprising a Raman-active material; and
   exposing an analyte adsorbed on one or both of the surface of the tapered indentation and the surface of the nanorod to an illumination signal to produce a Raman scattering signal,
   wherein an electromagnetic field incident from the upward direction is redirected and concentrated by a combination of a shape and the Raman-active material surface of the tapered indentation to facilitate one or both of production and detection of the Raman scattering signal emitted by the adsorbed analyte.

14. The method of SERS of claim 13, wherein providing the nanorod in a tapered indentation comprises:
   forming the tapered indentation in the substrate surface; and
   forming the nanorod within the tapered indentation.

15. The method of SERS of claim 13, further comprising:
   detecting the Raman scattering signal using a Raman signal detector, wherein one or both of the tapered indentation and the nanorod tip concentrate a field produced by the illumination signal to enhance the Raman scattered signal.

* * * * *